United States Patent
Wiss

(10) Patent No.: US 6,703,371 B1
(45) Date of Patent: Mar. 9, 2004

(54) PREPARATIONS FOR REDUCING OXYGEN CONSUMPTION DURING PHYSICAL EFFORTS

(76) Inventor: Oswald Wiss, Grellingerstrasse 94, Basel (CH), CH-4052

( * ) Notice: Subject to any disclaimer, the term of this patent is extended or adjusted under 35 U.S.C. 154(b) by 61 days.

(21) Appl. No.: 10/030,708

(22) PCT Filed: Jul. 21, 2000

(86) PCT No.: PCT/CH00/00400
§ 371 (c)(1),
(2), (4) Date: Jan. 14, 2002

(87) PCT Pub. No.: WO01/08680
PCT Pub. Date: Feb. 8, 2001

(30) Foreign Application Priority Data

Jul. 28, 1999 (CH) .............................................. 1388/99

(51) Int. Cl.⁷ .......................... A61K 31/00; A61K 31/70
(52) U.S. Cl. .......................... 514/23; 514/53; 536/1.11; 544/26; 544/32; 544/34; 544/114; 544/276; 546/44; 540/495; 549/6
(58) Field of Search .......................... 536/1.11; 514/23, 514/53; 544/26, 32, 34, 276, 114; 546/44; 540/495; 549/6

(56) References Cited

U.S. PATENT DOCUMENTS

| 4,647,450 A | * | 3/1987 | Peters et al. .................. 424/48 |
| 5,039,668 A | | 8/1991 | Colina |
| 5,292,538 A | | 3/1994 | Paul et al. |

FOREIGN PATENT DOCUMENTS

| EP | 0 087 068 | 8/1983 |
| EP | 0 482 715 | 4/1992 |
| FR | 2 704 392 | 11/1994 |
| JP | 52143255 | 11/1977 |
| JP | 02078624 | 3/1990 |
| JP | 02078625 | 3/1990 |
| JP | 5124974 | 5/1993 |
| JP | 7330583 | 12/1995 |
| WO | WO 90/02489 | 3/1990 |
| WO | WO 98/08521 | 3/1998 |

OTHER PUBLICATIONS

U.S. patent application Ser. No. 09/824,8010, Oswald Wiss, filed Apr. 4, 2001.
Monti et al., "The Actions of flunitrazepam (Rohypnol®) on Heart and Respiratory Rates and Skin Potential Fluctuations during the Sleep Cycle in Normal Volunteers and Neurotic Patients with Insomnia", Physchopharmacologia (Berl.) 43:187–190 (1975).
Matsukawa et al., "I.m. midazolam as premedication produces a concentration–dependent decrease in core temperature in male volunteers", British Journal of Anaesthesia 78:396–399 (1997).
Griffe et al., "Étude des efféts du diazépam sur la consommation d'oxygéne" Ann. Aneth. France, XX, 1, 37–40 (1979); with English language summary at p. 40.

\* cited by examiner

Primary Examiner—Samuel Barts
Assistant Examiner—Ganapathy Krishnan
(74) Attorney, Agent, or Firm—Leydig, Voit & Mayer, Ltd.

(57) ABSTRACT

The invention relates to pharmaceutically active substances from the group comprising midazolam and compounds with a methyl-substituted nitrogen atom that is the ring atom of a nitrogenous heterocycle. These substances are used to reduce the oxygen consumption during a physical activity. They can be administered together with an effective amount of D-glucose, D-maltose, ethanol, a glucogenic amine, a glucogenic amino acid or an amino acid metabolizable via glyoxylate or a dipeptide or a pharmaceutically acceptable salt of such an amino acid and an effective amount of thiamine, of a pharmaceutically acceptable thiamine salt or of a combination of folic acid and cyanocobalamine, with the proviso that the third component is thiamine or a pharmaceutically acceptable thiamine salt if the second component is D-glucose, D-maltose, a glucogenic amine, a glucogenic amino acid non-metabolizable via glyoxylate, or a dipeptide or a pharmaceutically acceptable salt of such an amino acid.

27 Claims, No Drawings

PREPARATIONS FOR REDUCING OXYGEN CONSUMPTION DURING PHYSICAL EFFORTS

The present invention relates to the novel use of certain compounds, in particular active pharmaceutical ingredients, for the manufacture of products with oxygen-sparing action during physical work, and to novel preparations with this action.

It is known that muscle glycogen is dependent on the diet and that only certain dietary constituents are suitable for its synthesis and are effective in varying degree. As a prerequisite for their efficacy it is necessary during their metabolic conversion for glucose or glucogenic metabolites to be formed. Efficacy is restricted de facto to carbohydrates and proteins, a further necessary prerequisite being that they are rapidly broken down into their constituents in the elementary tract and, during this, glucose and glucogenic amino acids are liberated and are able to have a beneficial effect on muscular glycogen synthesis.

In addition to glycogen, fats are available to the muscle and can be utilized alone or together with the glycogen. Glycogen and fats differ, however, in that glycogen contrasts with fats in that it requires no oxygen for energy production because the formation of glucose from glycogen is subject to an anaerobic metabolic sequence during which fatty acids liberated from fats undergo aerobic utilization.

The work capacity during physical activity, especially sustained work, is limited by the individual oxygen uptake capacity and the maximum individual heart rate. However, only part of the oxygen uptake is used for mechanical work, whereas a larger proportion serves to produce heat. The efficiency of mechanical work may vary within wide limits but averages only about 20%.

Active ingredients which reduce the oxygen demand for the same mechanical exertions increase the work capacity. Breakdown of the glycogen stored in muscle makes an increase in work capacity possible in the natural way in this sense. After the breakdown has taken place, the glycogen is formed anew during the resting period, provided that suitable nutrients such as easily digestible carbohydrates or meat from young animals and fish are consumed. On the other hand, nutrients administered shortly before or during the physical work have no effect on oxygen consumption or have an adverse effect inasmuch as they increase the oxygen demand for the same work. These interactions are attributable to additional oxygen demand caused by digestion, absorption and anabolism.

Besides these known associations, it has been found, surprisingly, that the oxygen consumption induced by mechanical work is also influenced by changes in the atmospheric pressure. It has been found in this connection that a fall in pressure of 1 mbar on average increases the oxygen demand by about 4%, which means that the work capacity may be considerably reduced under the influence of a low-pressure zone. No explanation for this effect is known. However, it is to be assumed that a change in the carbon dioxide content in the blood might be responsible for the changes in the oxygen demand because it is known that the alveolar carbon dioxide concentration rises when the atmospheric pressure falls.

Table 1a shows the results obtained in the period from Feb. 13 to Mar. 6, 1999, with a male subject in good physical condition under standard conditions. The subject was required each morning in the fasting state to perform successively (without interruption) at mechanical power output of 100 W, 125 W and 150 W, each lasting 10 minutes (total test duration 30 minutes each time). A bicycle ergometer from Ergo Fit (Pirmasens, Germany) was used for this, and the required work was controlled at 60 pedal revolutions per minute in each case (controlled by a metronome from Seiko, Japan) by means of an eddy current brake. A heart rate computer from Polar Electro (Kempele, Finland) was used for continuous measurement of the heart rate; the atmospheric pressure was measured by an electronic barograph from Altitude Instrumentation (Paris, France) with a resolution of 0.1 mbar; the temperature and relative humidity were measured by an electronic thermohygrometer. The heat production induced by mechanical exertion was calculated from the changes in the heart rate. An alternative possibility is also to determine it on the basis of the increase in humidity caused by the perspiration (the tests are carried out in a closed room) or reduction in weight (1 g of water=2.26 kJ). The subject received a high-carbohydrate diet mainly composed of pasta together with meat from young animals (veal, chicken, fish), in order to ensure an adequate supply of protein, throughout the three-week duration of the test. The values indicated in table 1a for the "average heart rate" are in each case averages over the 30-minute duration of the test; relative values for the oxygen consumption were established on the basis of the heart rates in a known manner, and the relative values indicated in Table 1a are based on the oxygen consumption on the first day (=100%); the values listed in the column "heat production" in Table 1a give the percentage deviation of the heat production, established on the basis of the perspiration, from the average from all the tests.

TABLE 1a

Effect of changes in the atmospheric pressure on the oxygen consumption induced by physical work

| Date 1999 | Atmospheric pressure (mbar) | Average heart rate (per minute) | Relative oxygen consumption | Relative humidity at start | Relative humidity at end | Relative humidity increase | Heat production* (%) |
|---|---|---|---|---|---|---|---|
| 2/13 | 1028.1 | 78.4 | 100% | 34% | 36% | 2% | −61 |
| 2/14 | 1029.4 | 83.8 | 108% | 33% | 35% | 3% | −31 |
| 2/15 | 1026.1 | 116.8 | 178% | 32% | 46% | 14% | +20 |
| 2/16 | 1014.9 | 109.6 | 164% | 33% | 43% | 10% | +5 |
| 2/17 | 1012.9 | 114.8 | 174% | 34% | 48% | 14% | +16 |
| 2/18 | 1015.6 | 116.8 | 178% | 35% | 48% | 13% | +20 |
| 2/19 | 1021.7 | 109.0 | 162% | 35% | 46% | 11% | +4 |
| 2/20 | 1016.8 | 122.4 | 188% | 36% | 52% | 16% | +32 |
| 2/21 | 1014.8 | 123.5 | 192% | 41% | 58% | 17% | +34 |

TABLE 1a-continued

Effect of changes in the atmospheric pressure
on the oxygen consumption induced by physical work

| Date 1999 | Atmospheric pressure (mbar) | Average heart rate (per minute) | Relative oxygen consumption | Relative humidity at start | at end | increase | Heat production* (%) |
|---|---|---|---|---|---|---|---|
| 2/22 | 1003.3 | 115.1 | 174% | 40% | 54% | 14% | +16 |
| 2/23 | 1011.6 | 102.1 | 148% | 35% | 45% | 10% | −11 |
| 2/24 | 1010.3 | 116.8 | 178% | 34% | 48% | 14% | +20 |
| 2/25 | 1019.3 | 79.3 | 102% | 36% | 38% | 2% | −59 |
| 2/26 | 1021.4 | 82.7 | 110% | 34% | 38% | 4% | −52 |
| 2/27 | 1016.1 | 123.5 | 190% | 33% | 48% | 15% | +34 |
| 2/28 | 1024.3 | 75.6 | 96% | 36% | 39% | 3% | −67 |
| 3/1 | 1024.6 | 115.6 | 176% | 36% | 49% | 13% | +17 |
| 3/2 | 1019.5 | 113.5 | 172% | 38% | 55% | 17% | +13 |
| 3/3 | 1004.6 | 114.8 | 174% | 39% | 55% | 16% | +16 |
| 3/4 | 995.2 | 116.5 | 178% | 40% | 55% | 15% | +19 |
| 3/5 | 995.4 | 118.0 | 180% | 38% | 44% | 16% | +22 |
| 3/6 | 1002.3 | 113.3 | 170% | 35% | 48% | 14% | +12 |

*Deviations from the average of all the tests

It is known that the oxygen uptake can be determined by measuring the heart rate as a function of the mechanical exertion. This ergometric method is based on establishing the oxygen transport volume through the action of the heart. Since the stroke volume is essentially constant irrespective of the intensity of the mechanical work, and the increased oxygen demand caused by the increase in work results in an increase in the heart rate, the quantity of the transported oxygen can be established by determining the additional heartbeats caused by the work. A 3-stage ergometer as recommended by the World Health Organization (WHO) is used in physiology research institutes and fitness clubs around the world.

The working muscle utilizes glycogen and fatty acids together to obtain energy. Muscle glycogen is broken down anaerobically. Fatty acid breakdown is dependent on molecular oxygen. If the glycogen reserves are exhausted and only fats remain available, the oxygen demand increases and thus the heart rate does too. At constant exertion if muscle glycogen is present therefore the heart rate increases slightly after the start of the mechanical exertion and remains at a low level as long as glycogen is available. After it is exhausted, there is a renewed increase to a higher level which is to be ascribed to exclusive utilization of fats. The oxygen transport volume of the action of the heart can therefore be determined by establishing the number of heartbeats at two different physical exertions, which are, however, each kept constant, through mechanical work (of, for example, at least 5 minutes each) if the utilization of muscle glycogen for supplying energy is switched off during the test in favor of exclusive utilization of fats, by the muscle glycogen being either broken down completely directly before the determination method by physical exertion of the muscles involved in the mechanical work, or its oxygen-sparing reaction being blocked by administration of an effective dose of an agent with antidiabetic activity. The oxygen transport volume per action of the heart was found for the test person to be 36 ml of oxygen based on standard pressure. The oxygen transport volume can then be calculated from the difference of the mechanical work and the corresponding difference of the number of heartbeats, an efficiency of 20% being used as basis for the purpose of the present invention, on the assumption that one fifth of the oxygen uptake is utilized for mechanical work and the remainder for heat production. The metabolic oxygen demand for the utilization of 1 kcal is 200 ml.

As is evident from Table 1a, the oxygen consumption rose distinctly when the pressure fell and remained at an elevated level while the low pressure persisted. No correlation was found between the oxygen consumption and the weather-related relative humidity. On the other hand, the perspiration caused by the heat production (which can be found from the corresponding increase in the humidity in the closed room) showed changes substantially paralleling those with the oxygen consumption, i.e. it likewise grows when the pressure fell. It is conceivable that the effect of the atmospheric pressure on the heat production is caused by the thermoregulation system because a fall in pressure normally occurs together with a fall in temperature. A sudden rise in carbon dioxide in the blood may increase muscle tone through isometric contractions, which is a reaction which also occurs when the body temperature falls.

The substantially parallel changes in the number of heartbeats, the heat production and the oxygen demand which are induced by mechanical exertion are also evident from the results compiled in Table 1b, which were obtained in analogous tests with the same test subject (resting pulse rate of 50 min$^{-1}$) in a closed room of about 20 m$^3$ in 41-minute test periods with constant mechanical exertion in each case. The calculations were based on the relations that 1 g of water=2.26 kJ, and 20 kJ=1 l of oxygen (at atmospheric pressure).

TABLE 1b

Relations between heart function,
oxygen demand and heat production

| Physical power output (W) | 125 | 150 | 175 | 200 | Increase* |
|---|---|---|---|---|---|
| Average heart rate (min$^{-1}$) | 71.8 | 85.8 | 99.8 | 125.8 | |
| Number of heartbeats induced by physical exertion | 893 | 1468 | 2042 | 3108 | 3.5 |
| Increase in the relative humidity by (%) | +5 | +9 | +15 | +20 | 4.0 |
| Water loss through perspiration (l) | 0.2 | 0.3 | 0.5 | 0.7 | 3.5 |
| Energy for heat production (kJ) | 438 | 661 | 1041 | 1522 | 3.5 |

TABLE 1b-continued

Relations between heart function,
oxygen demand and heat production

| Physical power output (W) | 125 | 150 | 175 | 200 | Increase* |
|---|---|---|---|---|---|
| Oxygen demand for heat production (1) | 21 | 31 | 50 | 72 | 3.5 |

*Ratio of the values at power outputs of 200 W and 125 W

A number of products which contain firstly energy-supplying components and secondly the vitamins necessary for metabolization thereof and which are intended to ensure optimal energy intake, maintain anabolism or combat vitamin deficiency have already been disclosed. In addition, various pharmaceutical products which, besides active pharmaceutical ingredients, may also contain vitamins and carbohydrates, proteins or ethanol are known. However, the previously disclosed products usually neither aim at nor succeed in reducing the oxygen consumption.

For example, U.S. Pat. No. 5,292,538 describes a fructose/glucose/protein mixture which, besides glucose polymers, fructose, partially hydrolyzed proteins, and, where appropriate, a lipid source, contains a magnesium complex and vitamins such as vitamin A, $B_1$, $B_2$, $B_5$, $B_6$, $B_{12}$, C, D, E, folic acid, niacinamide and biotin and which is intended to improve endurance performance and anabolism.

WO-A 90/02489 discloses an energy-supplying dietary product which is intended, by combining fast and slow sugars, to make an immediate and sustained energy contribution possible and which is provided with a coating of vitamin $B_1$ and/or $B_2$-containing chocolate.

FR-A 2 704 392 discloses an absorbable supplementary food for improving physical and mental work capacity which contains magnesium and vitamins C and $B_1$ together with a carrier which may preferably consist of cellulose, dextrose, magnesium stearate and carrot powder. The intention in this case is to utilize the fact that vitamin C increases the work capacity of the muscles and, on the other hand, magnesium and vitamin $B_1$ are required for enzymatic breakdown of sugars and fats. In addition, the presence of magnesium is said to reduce the oxygen consumption.

EP-A 0 087 068 discloses a nutritional supplement which contains selenium, cysteine, L-tryptophan, L-tyrosine and, if required, other ingredients such as fructose,, vitamin $B_1$, vitamin C and calcium salts and which is said to be suitable for replacing the essential nutritional constituents which are exhausted as a result of excessive alcohol consumption.

U.S. Pat. No. 5,039,668 describes a composition for treating vitamin deficiencies and as a cough suppressant which, besides liquid bee honey, histidine, lysine, tryptophan and calcium or iron salts, contains vitamins such as, for example, vitamin $B_{12}$ and folic acid, or vitamins $B_1$, $B_6$ and $B_{12}$, and niacin.

EP-A 0 482 715 proposes a composition based on protein-free carbohydrates and vegetable fats together with essential amino acids which is intended to provide a balanced supply of nutrients and have an immuno-stimulant effect and which moreover—owing to specific ratios of the essential amino acids—is intended to make it possible for the value of the NNU (net nitrogen utilization) to be higher. The proposed composition contains—besides the amino acids isoleucine, leucine, lysine, methionine, phenylalanine, threonine, tryptophan and valine—a carbohydrate from the group consisting of sucrose, maltose and sorbitol, a highly unsaturated vegetable fat from the group consisting of safflower oil, sunflower oil and corn oil, and vitamins A, $B_1$, $B_2$, $B_6$, $B_{12}$, C, D, K, biotin, folic acid, α-tocopherol, nicotinamide and pantothenic acid.

JP-A 07/330583 discloses a liquid preparation which is suitable as enteral nutrient for patients after surgical operations or burns and which, besides amino acids, may preferably also contain mineral salts, dextrin, soybean oil and vitamin A, $B_1$, $B_2$, $B_6$, $B_{12}$, C, D, E, K, folic acid and biotin.

JP-A 05/124974 proposes a preparation based on Fomes japonicus, which is intended to promote breakdown of the glycogen stored in the liver. It can be prepared, for example, in the form of a beverage which, besides the fungal extract, may also contain maltose, oligo-saccharides, folic acid, vitamin C, vitamin $B_{12}$ and iron.

JP-A 02/078624 discloses the use of an extract from the fibers of bamboo shoots for treating rheumatism and describes a preparation which, besides the extract, also contains ethanol, vitamin $B_1$ and vitamin L.

JP-A 02/078625 describes the use of an extract from Adenophora triphylla together with vitamin $B_1$ for treating pollinosis, and discloses a preparation in ethanol.

JP-A 52/143255 proposes, for masking the taste of medicinal substances, a medicinal beverage which, besides a medicinal substance such as garlic, ginseng, cranesbill, vitamin A, $B_1$, $B_2$ and the like, contains a beer obtained by top fermentation, and has an alcohol contents of 0.2 to 3% by weight.

WO-A 98/08521 furthermore discloses products which contain (a) an effective amount of D-glucose, D-maltose, ethanol, a glucogenic amine, an amino acid which is glucogenic or can be metabolized via glyoxylate, or a dipeptide or pharmaceutically acceptable salt of such an amino acid as first component and (b) an effective amount of thiamine, a pharmaceutically acceptable thiamine salt or a combination of folic acid and cyanocobalamin as second component, with the proviso that the second component is thiamine or a pharmaceutically acceptable thiamine salt if D-glucose, D-maltose, a glucogenic amine, a glucogenic amino acid which cannot be metabolized via glyoxylate, or a dipeptide or pharmaceutically acceptable salt of such an amino acid is used as first component. The disclosed products reduce the oxygen demand during physical work and their effect is based on their counteraction of the increase in the oxygen consumption caused by breakdown of the glycogen reserves.

It has now been found, surprisingly, that pharmaceuticals which have a nitrogen-containing heterocycle and in which at least one nitrogen atom present in the ring has a methyl substituent, and in addition midazolam reduce the oxygen consumption caused by mechanical work, and that they are moreover able to counteract in particular the increase in the oxygen consumption caused by low atmospheric pressure or a fall in pressure too. They are therefore suitable for considerably improving the efficiency of mechanical work, whereby the oxygen demand can be markedly reduced for the same mechanical work. Since an increased oxygen demand results in an increase in the heart rate and increased perspiration (which is caused by increased heat production), said pharmaceuticals are also able at the same time to reduce the heart rate and perspiration or heat production.

It is known that most of the oxygen intake in humans is used for heat production in order to maintain the body temperature. It is assumed that the heat production in periods of rest may vary by a factor of about 4, depending on the ambient temperature, whereas it may rise by a factor of about 10 as a result of heavy work at constant ambient temperature.

The cause of the effect found according to the invention is not known. However, it appears at least partly attributable to the fact that less oxygen is consumed for heat production and thus, on the one hand, a higher proportion of oxygen is available for physical work and, on the other hand, the perspiration is additionally reduced. It may therefore be assumed that the compounds might reduce or prevent the effect of carbon dioxide on heat production.

The invention therefore relates to the use of a pharmaceutically active ingredient from the group comprising midazolam and compounds with a methyl-substituted nitrogen atom which is a ring atom of a nitrogen-containing heterocycle for the manufacture of a product for reducing the oxygen consumption during physical work. Owing to the described connection between heart rate, oxygen demand and heat production (or perspiration), these active ingredients and products are suitable not only for reducing the increase in the oxygen demand induced by physical work but also for reducing the increase in the heart rate induced by physical work and for reducing the increase in heat production (or perspiration) induced by physical work.

Administration of the products which can be used according to the invention is indicated in all circumstances where the oxygen demand limits physical work capacity, especially when the oxygen uptake capacity is reduced owing to pathological changes in the cardiovascular system and the lungs, in the elderly, in the event of physical activity after intake of food and at altitude, in cases of fatigue caused by an increased oxygen demand through the influences of weather and for preventing unwanted side effects of drugs, in particular of tranquilizers, hypnotics, antidepressants and neuroleptics, on the oxygen demand. They are suitable for prophylactic or therapeutic use and should preferably be taken, depending on the administration form, at least about half an hour before the desired onset of action.

The active pharmaceutical ingredients suitable according to the invention may be, for example, alkaloids or alkaloid-analog compounds. However, it is in principle immaterial for the effect found according to the invention whether the compounds have an alkaloid-like structure, whether the substances are synthetic or naturally occurring or whether they are already known for another medical indication. The crucial point is—apart from the midazolam which is surprisingly likewise effective—on the contrary that they have an N heterocycle and at least one methyl group on a ring nitrogen atom.

The effect found according to the invention is moreover independent of known therapeutic effects and is not restricted to compounds with a particular medical indication. This is because it has been found that antitussives such as dihydrocodeine, noscapine, codeine and dextromethorphan, analgesics such as morphine and dihydrocodeine, anesthetics such as cocaine, hypnotics such as midazolam and flunitrazepam, antihistamines such as cyproheptadine, clemastine and carbimazole, tranquilizers such as diazepam, antidepressants such as dibenzepin and clothiapine, neuroleptics such as thioridazine, sedatives such as zopiclone, and the like are suitable. The compounds suitable according to the invention are moreover usually effective used in very small amounts; for example, in the case of known active pharmaceutical ingredients dosages which are about 2 powers of ten lower than for the previously known medical indications are frequently adequate.

On the other hand, it has been found that active ingredients with identical known medical indications and/or similar structure show no oxygen-sparing action or even have antagonistic activity if they do not have a methyl- substituted ring nitrogen atom. For example, the oxygen demand after administration of doxylamine, oxazepam, chlordiazepoxide, bromazepam, nitrazepam, imipramine, trimipramine, amitriptyline, opipramol, clomipramine, chlorprothixene, lorazepam or flupentixol is not reduced but is even occasionally increased. The latter has been observed in particular for tranquilizers, anti-depressants and neuroleptics, and it has been found that the increase in the oxygen demand caused by their administration can be prevented by additional administration of compounds suitable according to the invention.

The pharmaceutically active ingredients suitable according to the invention can be used as such or in the form of their pharmaceutically acceptable salts. They may be monocyclic compounds or, preferably, have polycyclic ring structures with bridged and/or fused rings. Suitable active ingredients may in particular have an N-methyl-substituted amine or amide group in a ring. The N heterocycle carrying the N-methyl group may be a saturated, partially unsaturated or aromatic ring, and active ingredients with a saturated or partially unsaturated, nonaromatic N-methyl-substituted N heterocycle are usually preferred.

Active ingredients which may be mentioned in particular as suitable according to the invention are:

compounds which have an N-methyl-substituted piperidine ring which may be saturated or partially unsaturated (for example N-methyl-piperidine derivatives with cyproheptadine, thioridazine and zopiclone) and/or may be part of a 2-methyl-2-azabicyclo[3.3.1]nonane structure (especially N-methylmorphinan derivatives such as dihydrocodeine, codeine, morphine, thebaine and dextromethorphan) or 2-methyl-1,2,3,4-tetrahydroisoquinoline structure (such as, for example, noscapine);

compounds with an N-methyl-substituted diazepine ring, in particular N-methylbenzodiazepines such as diazepam, flunitrazepam, dibenzepin and clobazam;

compounds with an N-methyl-substituted piperazine ring such as, for example, clothiapine;

compounds with an N-methyl-substituted pyrrolidine ring such as, for example, clemastine;

compounds with an N-methyl-substituted imidazole ring such as, for example, carbimazole and N-methylpurine derivatives such as caffeine;

compounds with an N-methyl-substituted pyrimidine ring such as, for example, caffeine.

Active ingredients which can particularly preferably be used according to the invention are: dextromethorphan, cyproheptadine, clothiapine, diazepam, midazolam, flunitrazepam, clemastine, dibenzepin, thioridazine, zopiclone, carbimazole, codeine and caffeine.

Pharmaceutical products can be manufactured in a manner which is known or known per se with use of conventional excipients. All conventional modes and forms of administration are suitable in principle, but it should be noted that the commercially available products mostly have too high a dose for the present use.

If desired, the pharmaceutically active ingredients or their pharmaceutically acceptable salts can be administered in the form of an aqueous solution or suspension. However, preference is given to products containing gelling agents, suitable gelling agents being gellable polymeric carbohydrates such as agar-agar or pectin or gellable proteins, in particular gelatin. This is because it has been found that it is often possible on use of a gelling agent such as gelatin to reduce the dose, and the activity is less affected by hydrophilic or lipophilic nature of the active ingredient, whereas it is possible and preferred in general to use lipophilic active ingredients in the absence of a gelling agent.

Products containing gelling agents can be manufactured in a manner known per se, for example by mixing an aqueous solution or suspension of the active ingredient or its salt with gelling agent and gelling it, or processing a solution or suspension of the active ingredient or its salt, which contains gelling agent, by spraying to give beadlets, preferably gelatin beadlets. Methods suitable for manufacturing beadlets are known to the skilled worker, for example from the manufacture of vitamin A gelatin beadlet. The beadlets can, if desired, be administered as such or be further processed in a manner known per se to give suitable administration forms.

The products may preferably contain, besides the pharmaceutically active ingredient and an optional gelling agent, also the combinations of components disclosed in WO-A 98/08521, which counteract the increase in the oxygen consumption caused by breakdown of the glycogen reserves. It is possible in this way to achieve an optimal oxygen-sparing action in every case, irrespective of whether an increased oxygen consumption is caused by a breakdown of the glycogen reserves, by low atmospheric pressure or by drugs.

The invention therefore likewise relates to a product for reducing the oxygen consumption during physical work, comprising (a) as first component an effective amount of a pharmaceutically active ingredient from the group comprising midazolam and compounds with a methyl-substituted nitrogen atom which is a ring atom of a nitrogen-containing heterocycle, (b) as second component an effective amount of D-glucose, D-maltose, ethanol, a glucogenic amine, an amino acid which is glucogenic or can be metabolized via glyoxylate, or a dipeptide or pharmaceutically acceptable salt of such an amino acid and (c) as third component an effective amount of thiamine, a pharmaceutically acceptable thiamine salt or a combination of folic acid and cyanocobalamin, with the proviso that the third component is thiamine or a pharmaceutically acceptable thiamine salt when the second component is D-glucose, D-maltose, a glucogenic amine, a glucogenic amino acid which cannot be metabolized via glyoxylate, or a dipeptide or pharmaceutically acceptable salt of such an amino acid.

The term "dipeptide" comprises for the purpose of the present invention the dipeptides of amino acids which are glucogenic or can be metabolized via glyoxylate, in particular dipeptides of two identical amino acids such as H-Gly-Gly-OH, H-Ser-Ser-OH and H-Glu-Glu-OH. The term "amino acid which can be metabolized via glyoxylate" comprises for the purpose of the present invention in particular amino acids suitable for nucleic acid synthesis.

According to a preferred aspect, the products may contain as second component D-glucose, D-maltose, a glucogenic amine, an amino acid which is glucogenic or can be metabolized via glyoxylate, or a dipeptide or pharmaceutically acceptable salt of such an amino acid and be gelled with a gelling agent. The gelling agent which is preferably used is a gellable polymeric carbohydrate, in particular agar-agar or pectin, if the second component is D-glucose or D-maltose, or a gellable protein, in particular gelatin, if the second component is an amino acid which is glucogenic or can be metabolized via glyoxylate, or a dipeptide or pharmaceutically acceptable salt of such an amino acid. Products with gelatin are particularly preferred.

The products may also preferably contain pyridoxine (vitamin $B_6$) or a pharmaceutically acceptable pyridoxine salt (for example pyridoxine hydrochloride), ascorbic acid (vitamin C) or a pharmaceutically acceptable ascorbate, such as sodium ascorbate, and/or biotin (vitamin H).

According to a first embodiment, the combination product may preferably contain as second component D-glucose, D-maltose, a glucogenic amine, an amino acid which is glucogenic or can be metabolized via glyoxylate, or a dipeptide or pharmaceutically acceptable salt of such an amino acid, as third component thiamine or a pharmaceutically acceptable thiamine salt and, if desired, as further components a gelling agent, vitamin C and/or vitamin $B_{12}$. In place of pure D-glucose it is also possible to employ fruits or fruit products. Examples of other substances which can be used as second component are glucogenic amino acids such as L-alanine, L-serine, L-cysteine, L-cystine, L-glutamic acid, L-aspartic acid, L-arginine, L-ornithine, L-threonine, L-valine, L-isoleucine, L-proline, L-oxyproline, L-tryptophan, L-tyrosine, L-phenylalanine, L-methionine and L-histidine, amino acids which can be converted into glyoxylate, such as glycine, L-serine and L-glutamic acid, dipeptides of amino acids which are glucogenic or can be converted into glyoxylate, such as H-Gly-Gly-OH, H-Ser-Ser-OH and H-Tyr-Tyr-OH, pharmaceutically acceptable salts of amino acids which are glucogenic or can be converted into glyoxylate, such as monosodium L-glutamate and monosodium L-aspartate, and glucogenic amines such as L-glutamine and L-asparagine. When L-aspartic acid, L-aspartate, L-phenylalanine, L-tyrosine and/or L-tryptophan is used as second, and thiamine as third, component, the products may preferably additionally contain vitamin C, vitamin $B_{12}$ and, if desired, gelatin and/or vitamin $B_6$ (pyridoxine). It is usually preferred to use glycine, L-serine, L-glutamic acid (or L-glutamate) and/or dipeptides thereof, and they may preferably be employed together with folic acid, vitamin $B_{12}$ and/or gelatin.

According to another embodiment, the combination product of the invention may contain as second component ethanol, as third component thiamine or a pharmaceutically acceptable thiamine salt and as further components biotin or, according to an alternative embodiment, contain as second component ethanol or as third component a combination of folic acid and cyanocobalamin. In these two cases it is possible and preferred for the product to be in the form of an aqueous solution.

According to a particularly preferred embodiment, the combination products of the invention can contain a pharmaceutically active ingredient from the group comprising midazolam and compounds with a methyl-substituted nitrogen atom which is a ring atom of a nitrogen-containing heterocycle, such as, for example, caffeine, a compound from the group comprising H-Gly-Gly-OH, H-Ser-Ser-OH, H-Glu-Glu-OH, glycine, serine and glutamic acid (or glutamate) and, in addition, folic acid, cyanocobalamin and gelatin. Such combination products are also suitable for counter-acting an increase in the oxygen demand caused by administration of sucrose, sulfonylurea derivatives with antidiabetic activity, insulin, glucocorticoids etc., which can evidently be ascribed to the stimulation of anaerobic muscular ATP synthesis.

Concerning further combinations with vitamins, in suitable dosages of the second, third and any further components of the combination products, reference is made to the disclosure in WO-A-98/08521.

The N-methyl N heterocycles which can be used according to the invention are usually effective in doses of as little as about 1–5 mg or less, even if they are not combined with a gelling agent, whereas in the case of caffeine the doses preferably administered are about 10–100 mg, in particular about 25–57 mg. If the N-methyl N heterocyle is administered in combination with a gelling agent such as gelatin, however, the dose in the case of caffeine may be reduced to about 1–5 mg and in the case of the other N-methyl N heterocycles usually to about 0.1–1.0 mg or less.

The products obtainable according to the invention can, as already mentioned above, be made in a manner known per se into conventional liquid, solid or semi-solid dosage forms such as, for example, aqueous solutions or suspensions (for example as drinkable solution), effervescent powders, granules or tablets, beadlets and the like and, if desired, contain conventional pharmaceutically acceptable carriers, diluents or excipients such as sodium bicarbonate, citric acid, mannitol, talc, corn starch, glycerol monostearate, food colors, flavorings and the like. If desired, the pharmaceutically active ingredients, vitamins and energy-supplying substances can also be administered singly since it is not crucial for the oxygen-sparing and work-enhancing action whether the components are taken separately or together with a combination product.

Since both the pharmaceutically active ingredients and the combinations disclosed in WO-A 98/08521 are rapidly effective, the products which can be used according to the invention may be taken before or during physical work in order to achieve a reduction in the oxygen demand and thus an ergogenic effect. The present invention therefore provides a method for reducing the oxygen consumption during physical work through administration of the product obtainable according to the invention before and/or during the physical work, it being possible in the case of administration of a plurality of active components for the latter to be administered as combination product or separately but simultaneously.

The invention is illustrated further by the following examples. The relative values for the oxygen consumption stated in the examples were measured by the method mentioned in connection with table 1.

EXAMPLE 1

A male test subject in good physical condition carried out the series of tests described below under standardized conditions. Unless otherwise indicated, the tests each took place in the morning in the fasting state, with mechanical power outputs of 100 W, 125 W or 150 W being required in each case from the test subject during one or more 10-minute test periods. A bicycle ergometer from Ergo Fit (Kaiserslautern, Germany) was used for this, and the required work was controlled at 60 pedal revolutions per minute in each case (controlled by a metronome from Seiko, Japan) by means of an eddy current brake. A heart rate computer from Polar Electro (Kempele, Finland) was used for continuous measurement of the heart rate; the atmospheric pressure was measured by an electronic barograph from Altitude Instrumentation (Paris, France) with a resolution of 0.1 mbar; the temperature and relative humidity were measured by an electronic thermohygrometer. The "average heart rates" indicated in the tables are in each case averages of the particular test period. The test subject received a high-carbohydrate diet mainly composed of pasta, and meat of young animals (veal, chicken, fish) in order to ensure an adequate supply of protein, throughout the series of tests. Only 1 test was carried out on each day.

a) In a first series of tests, the activity of various N heterocycles was investigated, determining in each case the average heart rate, the oxygen consumption and the heat production during a 10-minute test period at a constant power output of 125 W. After a warm-up period of 5 minutes in each case firstly the heartbeats were recorded at a power output of 125 W during a 10-minute control test, then a pharmaceutically active ingredient was administered in the form of a dilute aqueous solution (20 ml of water) and, immediately thereafter, the actual test was carried out. The active ingredients and dosages used, and their effects on the heart rate, the oxygen demand and the heat production (stated as deviations from the average heat production over all the tests) are compiled in Table 2, the heat production being calculated on the basis of the change in the humidity in the closed test room. As shown by the results, midazolam and compounds having an N-methyl-substituted N heterocycle led even at low dosage to a marked reduction in the heart rate, the oxygen consumption and the heat production, whereas other pharmaceutically active ingredients which have no methyl groups on a ring nitrogen atom resulted in no significant effect or even brought about an increase in heat production.

b) In another series of tests, the antagonism between active and inactive substances was investigated, determining in each case the average heart rate, the oxygen consumption and the heat production during two 10-minute test periods with a constant power output of 100 W. After a warm-up period of 5 minutes in each case firstly the heartbeats were recorded at a power output of 100 W during a 10-minute control test, then a 1st dosage of an inactive substance (in 20 ml of water) were administered and immediately thereafter the effect on the heart rate, oxygen consumption and heat production was determined during a 10-minute test period; after a pause for 5 minutes, a 2nd dosage of an active substance (in 20 ml of water) was administered and again immediately thereafter its effect was determined during a second 10-minute test period. The substances and dosages used, and their effects on the heart rate and the oxygen demand are compiled in Table 3, where the changes in the oxygen consumption after the 2nd dose in each case relate to the changes in the oxygen consumption measured after the 1st dosage. The results show that the first dosage in each case led to a marked increase and the second dosage to a marked reduction in the heart rate and the oxygen consumption, the values after the second dosage in each case being in fact below the control values before the first dosage. Corresponding results were also measured for the heat production, where the 1st dosage led to an increase of 13–55% in heat production and the 2nd dosage led to a reduction of 26–45% in heat production. The active ingredients which can be used according to the invention are thus suitable for preventing an increase in the oxygen demand, the heart rate and the heat production caused by drugs.

TABLE 2

Effect of pharmaceutically active ingredients on the oxygen demand and heat production during physical activity

| Active ingredient | Average heart rate (per minute) | | Change in the oxygen demand | Heat production* |
|---|---|---|---|---|
| | before | after | | |
| No active ingredient | 106.1 | 109.1 | 0% | +6% |
| With oxygen-reducing effect: | | | | |
| 0.2 mg of codeine | 113.1 | 98.8 | −29% | −27% |
| 0.2 mg of dextromethorphan | 117.5 | 89.2 | −57% | −49% |

TABLE 2-continued

Effect of pharmaceutically active ingredients on the oxygen demand and heat production during physical activity

| Active ingredient | Average heart rate (per minute) before | Average heart rate (per minute) after | Change in the oxygen demand | Heat pro- duction* |
|---|---|---|---|---|
| 0.2 mg of cyproheptadine | 107.6 | 81.6 | −52% | −55% |
| 1 mg of clemastine | 120.6 | 102.2 | −37% | −30% |
| 5 mg of carbimazole | 120.3 | 104.9 | −30% | −26% |
| 1 mg of diazepam | 102.3 | 81.0 | −44% | −50% |
| 1 mg of midazolam | 104.5 | 83.4 | −42% | |
| 1 mg of flunitrazepam | 109.8 | 90.1 | −39% | −40% |
| 1 mg of dibenzepin | 100.3 | 83.6 | −33% | −41% |
| 1 mg of clothiapine | 112.0 | 86.4 | −51% | −49% |
| 1 mg of thioridazine | 120.3 | 104.9 | −31% | −26% |
| 1 mg of clobazam | 106.1 | 80.8 | −51% | −49% |
| 25 mg of caffeine | 110.8 | 97.1 | −26% | |
| 1 mg of zopiclone | 116.8 | 91.8 | | −44% |
| Without oxygen-reducing effect: | | | | |
| 4 mg of doxylamine | 109.5 | 109.5 | −6% | 0% |
| 1 mg of oxazepam | 112.6 | 116.5 | 0% | +7% |
| 1 mg of chlordiazepoxide | 104.0 | 110.2 | 0% | +14% |
| 1 mg of bromazepam | 114.8 | 118.2 | 0% | +6% |
| 1 mg of nitrazepam | 116.1 | 119.8 | 0% | +7% |
| 1 mg of imipramine | 109.5 | 110.9 | −2% | +3% |
| 1 mg of amitriptyline | 106.0 | 112.0 | 0% | +13% |
| 1 mg of opipramol | 111.4 | 112.0 | −5% | +1% |
| 1 mg of clomipramine | 112.8 | 117.5 | 0% | +9% |
| 1 mg of chlorprothixen | 106.1 | 112.0 | 0% | +13% |
| 1 mg of trimipramine | 108.6 | 109.8 | | +2% |

*Deviation from the average of all the tests disclosed in WO-A 98/08521 was investigated, in each case determining the average heart rate and the oxygen consumption during consecutive 10-minute test periods with a constant power output of 100 W. After a warm-up period of 5 minutes in each case firstly the heartbeats were recorded at a power output of 100 W during a 10-minute control test, then an active ingredient (as dilute aqueous solution, 1st dosage) and, in each case at an interval of 10 minutes, 2.5 g of sucrose (2nd dosage), further active ingredient (as dilute aqueous solution, 3rd dosage) and an amino acid/vitamin product containing 100 mg of sodium glutamate, 0.3 mg of folic acid, 5 $\mu$g of cyanocobalamin and 10 mg of gelatin (4th dosage) were administered, determining the effect on the heart rate and oxygen consumption during a 10-minute test period immediately after each administration. The active ingredients and amounts used, and the effects of the four dosages on the heart rate and oxygen demand are compiled in Table 4, where the changes in the oxygen consumption in each case relate to the changes in the oxygen consumption measured after the preceding dosage. The results show that the pharmaceutically active ingredients which can be used according to the invention are not on their own suitable for compensating for the increase in the heart rate and oxygen consumption caused by administration of sucrose; a reduction occurs only after administration of a product as disclosed in WO-A 98/08521.

TABLE 3

Antagonisms between active ingredients with and without an action reducing oxygen demand

| 1st dosage | 2nd dosage | Average heart rate (per minute) before | Average heart rate after 1st dosage | Average heart rate after 2nd dosage | Change in the oxygen consumption after 1st dosage | Change in the oxygen consumption after 2nd dosage |
|---|---|---|---|---|---|---|
| no active ingredient (control) | | 106.1 | 109.1 | 108.1 | | |
| 7 mg of oxazepam | 0.5 mg of codeine | 121.3 | 137.6 | 104.1 | +33% | −67% |
| 1 mg of lorazepam | 0.5 mg of codeine | 104.4 | 121.5 | 91.8 | +34% | −59% |
| 10 mg of chlorprotixen | 0.5 mg of codeine | 101.7 | 124.6 | 90.0 | +46% | −69% |
| 0.5 mg of flupentixol | 0.5 mg of codeine | 102.6 | 118.4 | 89.7 | +32% | −57% |
| 6 mg of amitriptyline + 2.5 mg of chlordiazepoxide | 0.5 mg of codeine | 97.0 | 112.7 | 86.5 | +31% | −52% |
| 6 mg of amitriptyline + 2.5 mg of chlordiazepoxide | 0.2 mg of dextromethorphan | 107.2 | 125.4 | 84.8 | +36% | −81% |
| 5 mg of chlordiazepoxide | 0.2 mg of cyproheptadine | 111.9 | 126.4 | 88.5 | +29% | −76% |
| 10 mg of amitriptyline | 0.2 mg of cyproheptadine | 83.6 | 119.3 | 87.6 | +71% | −63% |
| 7 mg of oxazepam | 1 mg of diazepam | 109.5 | 125.3 | 89.4 | +32% | −72% |
| 3 mg of bromazepam | 1 mg of diazepam | 118.0 | 129.3 | 97.0 | +23% | −65% |
| 10 mg of nitrazepam | 1 mg of diazepam | 121.0 | 131.4 | 102.1 | +21% | −59% |
| 50 mg of opipramol | 1 mg of dibenzepin | 111.5 | 118.0 | 88.3 | +14% | −59% |
| 25 mg of clomipramine | 1 mg of clothiapine | 113.7 | 134.8 | 100.0 | +42% | −70% |
| 50 mg of opipramol | 1 mg of clothiapine | 103.1 | 121.4 | 88.9 | +37% | −65% |
| 10 mg of imipramine | 1 mg of thioridazine | 98.1 | 109.5 | 81.5 | +23% | −56% | c) In another series of tests, the effect of additionally administered sucrose and amino acid/vitamim products as

TABLE 4

Synergism between pharmaceutically active ingredients and amino acid/vitamin products

| | | Average heart rate (per minute) after | | | | Change in oxygen consumption after | | |
|---|---|---|---|---|---|---|---|---|
| 1st Dosage | 3rd Dosage | 1st dos. | 2nd dos. | 3rd dos. | 4th dos. | 2nd dos. | 3rd dos. | 4th dos. |
| 0.2 mg of codeine | 0.2 mg of codeine | 73.0 | 107.3 | 108 | 82.9 | +69% | +2% | −50% |
| 0.2 mg of dextromethorphan | 0.2 mg of dextyromethorphan | 75.8 | 110.4 | 111 | 87.8 | +69% | +1% | −46% |
| 0.2 mg of cyproheptadine | 0.2 mg of cyproheptadine | 74.7 | 109.1 | 106.4 | 83.9 | +69% | −5% | −45% |
| 1 mg of diazepam | 1 mg of diazepam | 74.8 | 111.9 | 113.1 | 86.3 | +74% | +2% | −54% |
| 1 mg of midazolam | 1 mg of midazolam | 75.9 | 110.9 | 112.1 | 83.2 | +70% | +2% | −58% |
| 1 mg of dibenzepin | 1 mg of dibenzepin | 77.2 | 111.5 | 115 | 86.4 | +69% | 0% | −57% |
| 1 mg of clothiapine | 1 mg of clothiapine | 73.2 | 112.4 | 113.9 | 82.2 | +78% | +3% | −63% |
| 1 mg of thioridazine | 1 mg of thioridazine | 76.3 | 111.0 | 111.2 | 86.5 | +69% | 0% | −49% |

2nd dosage: 2.5 g of sucrose
4th dosage: 100 mg of Na glutamate, 0.3 mg of folic acid and 5 μg of cyanocobalamin in 10 mg of gelatin

EXAMPLE 2

In another series of tests under analogous test conditions as in Example 1, the dependence of the heart rate from the atmospheric pressure and the effect of diazepam at a constant mechanical power output of 125 W was investigated. Only 1 test was carried out on each day. The results compiled in Table 5 confirm that the heart rate and thus the oxygen consumption is increased in low pressure situations and this effect of the atmospheric pressure can be compensated by administering diazepam.

TABLE 5

Heart rate as a function of the atmospheric pressure with or without previous administration of diazepam

| Active ingredient | Atmospheric pressure (mbar) | Average heart rate (per minute) |
|---|---|---|
| No active ingredient | 1010.5 | 124 |
| No active ingredient | 1013.7 | 124 |
| No active ingredient | 1014.8 | 124 |
| No active ingredient | 1014.8 | 123 |
| No active ingredient | 1016.1 | 123 |
| No active ingredient | 1023.1 | 87 |
| No active ingredient | 1023.9 | 87 |
| No active ingredient | 1025.5 | 74 |
| No active ingredient | 1026.3 | 75 |
| No active ingredient | 1028.4 | 84 |
| 2 mg of diazepam | 1005.9 | 76 |
| 2 mg of diazepam | 1007.8 | 79 |
| 1 mg of diazepam | 1010.0 | 80 |
| 1 mg of diazepam | 1010.8 | 71 |
| 0.1 mg of diazepam + 4 mg of gelatin | 1011.0 | 77 |
| 0.02 mg of diazepam + 1 mg of gelatin | 1014.8 | 82 |
| 1 mg of diazepam | 1015.2 | 77 |
| 1 mg of diazepam | 1015.9 | 72 |
| 1 mg of diazepam | 1017.4 | 74 |
| 1 mg of diazepam | 1017.5 | 72 |
| 1 mg of diazepam | 1021.7 | 76 |
| 1 mg of diazepam | 1026.3 | 75 |

EXAMPLE 3

200 parts by weight of Gly-Gly, 3 parts by weight of folic acid, 0.05 parts by weight of cyanocobalamin, 1 part by weight of diazepam and 200 parts by weight of gelatin are dissolved by heating in 10 000 parts by weight of water. Gelatin beadlets are produced by spraying the solution and can be further processed to pharmaceutical use forms.

EXAMPLE 4

100 parts by weight of tyrosin, 50 parts by weight of thiamine, 50 parts by weight of pyridoxine, 100 parts by weight of ascorbic acid, 0.05 part by weight of cyanocobalamin, 1 part by weight of dextromethorphan and 200 parts by weight of gelatin are dissolved by heating in 10 000 parts by weight of water. Gelatin beadlets are produced by spraying the solution and can be further processed to pharmaceutical use forms.

EXAMPLE 5

150 mg of monosodium glutamate, 0.3 mg of folic acid, 5 μg of cyanocobalamin, 0.1 mg of codeine and 5 mg of gelatin are dissolved by heating in 1 ml of water and mixed with 9 ml of a 4% strength solution of ethanol in water. 10 ml of the solution corresponds to a single dose.

EXAMPLE 6

In analogy to Example 1, the effect of ascorbic acid, sucrose, glibenclamide and H-Arg-Asp-OH after administration on their own or after administration together with a caffeine/amino acid/vitamin combination product (containing 5 mg of H-Gly-Gly-OH, 250 μg of folic acid, 5 μg of cyanocobalamin, 1 mg of caffeine and 1 mg of gelatin and produced in analogy to Example 3) on the oxygen demand and heat production was investigated in 30-minute tests at a constant mechanical power output of 125 W. The results are compiled in Table 6, the oxygen consumption being calculated from the heart rate on the basis of a previously determined value of 29 ml of oxygen (at standard pressure) per contraction of the heart and the heat production being calculated from the water lost through perspiration (determined from the change in the humidity in the closed test room) on the basis of a heat of vaporization of 2.26 kJ per g of water. The results show that the combination product is suitable for compensating the increase in the oxygen consumption and heat production caused by the test substances.

TABLE 6

Prevention of a food- or medicament-related increase in the oxygen demand and the heat production during physical activity Effect*

| Test substances | Effect* on oxygen demand (l) | on heat production (kJ) |
|---|---|---|
| 500 mg of ascorbic acid | +19 | +380 |
| 500 mg of ascorbic acid + product A | −16 | −320 |
| 5 g of sucrose | +19 | +380 |
| 5 g of sucrose + product A | −11 | −220 |
| 2.5 mg of glibenclamide | +20 | +400 |
| 2.5 mg of glibenclamide + product A | −10 | −200 |
| 100 mg of H-Arg-Asp-OH | +13 | +260 |
| 100 mg of H-Arg-Asp-OH + product A | −7 | −100 |

*Change from control test without test substances
Product A: 5 mg of H-Gly-Gly-OH, 250 μg of folic acid, 5 μg of cyanocobalamin, 1 mg of caffeine and 1 mg of gelatin

TABLE 7

Increase in the activity through binding to gelatin

| | | Average heart rate (per minute) | | |
|---|---|---|---|---|
| 1st dosage | 2nd dosage | before | after 1st dos. | after 2nd dos. |
| 0.1 mg of diazepam + 5 mg of gelatin | | 89.4 | 66.6 | |
| 7 mg of oxazepam + 0.1 mg of diazepam + 5 mg of gelatin | | 81.9 | 66.6 | |
| 25 mg of imipramine + 0.1 mg of dibenzepin + 5 mg of gelatin | | 73.0 | 64.0 | |
| 25 mg of clomipramine + 0.1 mg of clothiapine + 5 mg of gelatin | | 100.5 | 79.1 | |
| 12.5 mg of trimipramine + 0.1 mg of clobazam + 5 mg of gelatin | | 74.0 | 63.0 | |
| 12.5 mg of trimipramine + 0.1 mg of zopiclone + 5 mg of gelatin | | 86.8 | 71.3 | |
| 12.5 mg of trimipramine + 0.02 mg of cyproheptadine + 5 mg of gelatin | | 78.9 | 57.0 | |
| 12.5 mg of trimipramine | 0.1 mg of clobazam + 5 mg of gelatin | 79.8 | 101.7 | 74.2 |
| 12.5 mg of trimipramine | 0.1 mg of zopiclon + 5 mg of gelatin | 81.7 | 97.0 | 72.1 |
| 10 mg of imipramine | 0.1 mg of dibenzepin + 5 mg of gelatin | 87.7 | 100.2 | 80.2 |

EXAMPLE 7

In tests analogous to Example 1, the tests indicated in Table 7 were carried out with gelatin products which were produced in analogy to Examples 3–5. After a warm-up period of 5 minutes in each case firstly the heartbeats were recorded at a mechanical power output of 100 W during a 10-minute control test, then the 1st dosage was administered and immediately thereafter the heart rate was measured in a 10-minute test period with a power output of 100 W. In the case of a 2nd dosage, this further administration and a second 10-minute test period take place with a power output of 100 W immediately following the first test period. The results in Table 7 show that the dosage of the active ingredients which can be used according to the invention can usually be reduced to distinctly less than 1 mg if they are administered in combination with gelatin. In addition, the results show that the active ingredients in these low dosages are able to compensate for the increasing effect of other medicaments on the oxygen consumption and heart rate, irrespective of whether the latter are administered together with the active ingredient which can be used according to the invention or separately.

What is claimed is:

1. A product for reducing the oxygen consumption during physical work, comprising (a) as first component an effective amount of a pharmaceutically active ingredient from the group comprising midazolam and compounds having a methyl-substituted nitrogen atom which is a ring atom of a nitrogen-containing heterocycle, (b) as second component an effective amount of D-glucose, D-maltose, ethanol, a glucogenic amine, an amino acid which is glucogenic or can be metabolized via glyoxylate, or a dipeptide or pharmaceutically acceptable salt of such an amino acid and (c) as third component an effective amount of thiamine, a pharmaceutically acceptable thiamine salt or a combination of folic acid and cyanocobalamin, with the proviso that the third component is thiamine or a pharmaceutically acceptable thiamine salt if the second component is D-glucose, D-maltose, a glucogenic amine, a glucogenic amino acid which cannot be metabolized via glyoxylate, or a dipeptide or pharmaceutically acceptable salt of such an amino acid.

2. The product of claim 1, wherein the pharmaceutically active ingredient is dextromethorphan, cyproheptadine, clothiapine, diazepam, midazolam, flunitrazepam, clemastine, dibenzepin, thioridazine, carbimazole, codeine, caffeine, dihydrocodeine, morphine, thebaine, noscapine, clobazam or a pharmaceutically acceptable salt thereof.

3. The product of claim 1 which is in the form of an aqueous solution or suspension or of a product containing a gelling agent.

4. The product of claim 1, which additionally comprises pyridoxine or a pharmaceutically acceptable pyridoxine salt, ascorbic acid or a pharmaceutically acceptable ascorbate, and/or biotin.

5. The product of claim 1 which comprises as second component D-glucose, D-maltose, a glucogenic amine, an amino acid which is glucogenic or can be metabolized via glyoxylate, or a dipeptide or pharmaceutically acceptable salt of such an amino acid, as third component thiamine or a pharmaceutically acceptable thiamine salt and, if desired, as further components a gelling agent, vitamin C and/or vitamin $B_{12}$.

6. The product of claim 5, which comprises as second component glycine, L-serine, L-glutamic acid and/or a dipeptide or pharmaceutically acceptable salt thereof and, if desired, as further components folic acid, vitamin $B_{12}$ and/or gelatin.

7. The product of claim 1, which comprises as second component ethanol, as third component thiamine or a pharmaceutically acceptable thiamine salt and as further component biotin.

8. The product of claim 1, which comprises as second component ethanol and as third component a combination of folic acid and cyanocobalamin.

9. The product of claim 3, wherein the gelling agent is in the form of gelatin beadlets.

10. The product of claim 2 which is in the form of an aqueous solution or suspension or of a product containing a gelling agent.

11. The product of claim 10, wherein the gelling agent is in the form of gelatin beadlets.

12. The product of claim 2 which additionally comprises pyridoxine or a pharmaceutically acceptable pyridoxine salt, ascorbic acid or a pharmaceutically acceptable ascorbate, and/or biotin.

13. The product of claim 2 which comprises as second component D-glucose, D-maltose, a glucogenic amine, an amino acid which is glucogenic or can be metabolized via glyoxylate, or a dipeptide or pharmaceutically acceptable salt of such an amino acid, as third component thiamine or a pharmaceutically acceptable thiamine salt and, if desired, as further components a gelling agent, vitamin C and/or vitamin $B_{12}$.

14. The product of claim 1, wherein the second component is an amino acid which can be metabolized via glyoxylate or a dipeptide or pharmaceutically acceptable salt of such an amino acid.

15. The product of claim 1, wherein the second component is a dipeptide of an amino acid which can be metabolized via glyoxylate.

16. The product of claim 1, wherein the second component is a dipeptide selected from the group consisting of H-Gly-Gly-OH, H-Ser-Ser-OH and H-Glu-Glu-OH.

17. The product of claim 2, wherein the second component is an amino acid which can be metabolized via glyoxylate or a dipeptide or pharmaceutically acceptable salt of such an amino acid.

18. The product of claim 3, wherein the second component is an amino acid which can be metabolized via glyoxylate or a dipeptide or pharmaceutically acceptable salt of such an amino acid.

19. The product of claim 9, wherein the second component is an amino acid which can be metabolized via glyoxylate or a dipeptide or pharmaceutically acceptable salt or such an amino acid.

20. The product of claim 1, wherein the third component is a combination of folic acid and cyanocobalamin.

21. The product of claim 2, wherein the third component is a combination of folic acid and cyanocobalamin.

22. The product of claim 3, wherein the third component is a combination of folic acid and cyanocobalamin.

23. The product of claim 9, wherein the third component is a combination of folic acid and cyanocobalamin.

24. The product of claim 1, wherein the first component is selected from the group consisting of dextromethorphan, cyproheptadine, clothiapine, diazepam, midazolam, flunitrazepam, clemastine, dibenzepin, thioridazine, carbimazole, codeine, caffeine, dihydrocodeine, morphine, thebaine, noscapine, clobazam and pharmaceutically acceptable salts thereof, the second component is an amino acid which can be metabolized via glyoxylate or a dipeptide or pharmaceutically acceptable salt of such an amino acid, and the third component is a combination of folic acid and cyanocobalamin.

25. The product of claim 24 which is in the form of an aqueous solution or suspension or of a product containing a gelling agent.

26. The product of claim 25, wherein the gelling agent is in the form of gelatin beadlets.

27. The product of claim 16, wherein the second component is H-Gly-Gly-OH.

* * * * *